US011006929B2

(12) United States Patent
Watanabe (10) Patent No.: US 11,006,929 B2
(45) Date of Patent: May 18, 2021

(54) OBJECT INFORMATION ACQUIRING APPARATUS AND SIGNAL PROCESSING METHOD

(71) Applicant: CANON KABUSHIKI KAISHA, Tokyo (JP)

(72) Inventor: Tadaki Watanabe, Nagoya (JP)

(73) Assignee: Canon Kabushiki Kaisha, Tokyo (JP)

( * ) Notice: Subject to any disclaimer, the term of this patent is extended or adjusted under 35 U.S.C. 154(b) by 538 days.

(21) Appl. No.: 16/065,459

(22) PCT Filed: Jan. 13, 2017

(86) PCT No.: PCT/JP2017/001051
§ 371 (c)(1),
(2) Date: Jun. 22, 2018

(87) PCT Pub. No.: WO2017/126436
PCT Pub. Date: Jul. 27, 2017

(65) Prior Publication Data
US 2019/0000423 A1    Jan. 3, 2019

(30) Foreign Application Priority Data
Jan. 21, 2016 (JP) .............................. JP2016-009864

(51) Int. Cl.
*A61B 8/00*   (2006.01)
*A61B 8/08*   (2006.01)
(Continued)

(52) U.S. Cl.
CPC .......... *A61B 8/5207* (2013.01); *A61B 5/0095* (2013.01); *A61B 8/0825* (2013.01);
(Continued)

(58) Field of Classification Search
CPC ....... A61B 8/5207; A61B 8/0821; A61B 8/14; A61B 8/406
See application file for complete search history.

(56) References Cited

U.S. PATENT DOCUMENTS 6,374,674 B1   4/2002   Mine
7,440,543 B2   10/2008  Morton
(Continued)

FOREIGN PATENT DOCUMENTS

CN   1753029 A   3/2006
CN   1802553 A   7/2006
(Continued)

OTHER PUBLICATIONS

Jun. 1, 2020 Chinese Official Action in Chinese Patent Appln. No. 201780006939.0.
(Continued)

*Primary Examiner* — Joseph M Santos Rodriguez
(74) *Attorney, Agent, or Firm* — Venable LLP (57) ABSTRACT

An object information acquiring apparatus comprising: a processor generating image data representing characteristic information on an object, based on signals acquired by receiving an acoustic wave generated from an object by a plural light irradiations; and a display controller allowing a display to display an image, wherein the display controller performs first display in which an image is displayed in parallel with irradiation and second display in which an image is displayed based on more signal than in the first display, and the processor acquires the characteristic information for a smaller number of units of reconstruction when generating image data.

19 Claims, 5 Drawing Sheets

(51) Int. Cl.
*A61B 8/14* (2006.01)
*A61B 5/00* (2006.01)
*G06T 7/11* (2017.01)
*G01S 7/52* (2006.01)
*G01S 15/89* (2006.01)
*G06T 11/00* (2006.01)

(52) U.S. Cl.
CPC ............... *A61B 8/14* (2013.01); *A61B 8/406* (2013.01); *A61B 8/4461* (2013.01); *A61B 8/4494* (2013.01); *G01S 7/52053* (2013.01); *G01S 7/52085* (2013.01); *G01S 15/8968* (2013.01); *G06T 7/11* (2017.01); *G06T 11/003* (2013.01); *A61B 5/0091* (2013.01); *G06T 2207/20104* (2013.01)

(56) References Cited

U.S. PATENT DOCUMENTS

| | | | |
|---|---|---|---|
| 7,724,868 | B2 | 5/2010 | Morton |
| 7,734,119 | B2 | 6/2010 | Cheryauka et al. |
| 7,929,663 | B2 | 4/2011 | Morton |
| 8,920,321 | B2 | 12/2014 | Yoda |
| 9,766,211 | B2 | 9/2017 | Oishi |
| 9,974,440 | B2 | 5/2018 | Tsujita |
| 10,663,436 | B2 | 5/2020 | Oishi |
| 2006/0061570 | A1 | 3/2006 | Cheryauka et al. |
| 2006/0203961 | A1 | 9/2006 | Morton |
| 2006/0269113 | A1 | 11/2006 | Gundel et al. |
| 2009/0010382 | A1 | 1/2009 | Morton |
| 2010/0303295 | A1 | 12/2010 | Morton |
| 2011/0098550 | A1 | 4/2011 | Yoda |
| 2012/0302864 | A1 | 11/2012 | Yoda |
| 2013/0035570 | A1 | 2/2013 | Miyasato |
| 2013/0312526 | A1 | 11/2013 | Oishi |
| 2014/0107462 | A1 | 4/2014 | Wanda |
| 2014/0371571 | A1 | 12/2014 | Tsujita |
| 2017/0350869 | A1 | 12/2017 | Oishi |

FOREIGN PATENT DOCUMENTS

| | | |
|---|---|---|
| CN | 102908164 A | 2/2013 |
| CN | 103354731 A | 10/2013 |
| JP | 2010-022812 A | 2/2010 |
| JP | 2012-179348 A | 9/2012 |
| JP | 2013-027604 A | 2/2013 |
| JP | 2013-176414 A | 9/2013 |
| WO | 2004/097344 A2 | 11/2004 |

OTHER PUBLICATIONS

Jul. 24, 2018 International Preliminary Report on Patentability in International Patent Application No. PCT/JP2017/001051.

Apr. 10, 2017 International Search Report and Written Opinion in International Patent Appln. No. PCT/JP2017/001051.

Jan. 8, 2021 Chinese Official Action in Chinese Patent Appln. No. 201780006939.0.

OBJECT INFORMATION ACQUIRING APPARATUS AND SIGNAL PROCESSING METHOD

TECHNICAL FIELD

The present invention relates to an object information acquiring apparatus and a signal processing method.

BACKGROUND ART

Photoacoustic imaging is an optical imaging technique using light. In the photoacoustic imaging, a living organism that is an object is irradiated with pulsed light, and transducers receive acoustic waves generated by a test segment having absorbed energy of the pulsed light. Then, receive signal output from the transducers are analyzed to acquire optical characteristic information on the interior of the living organism as image data.

PTL 1 discloses an apparatus in which a breast is held in a sandwiching manner using a holding member and in which transducers receives acoustic waves while performing two-dimensional scans over the holding member. Two-dimensional scans by the transducer allow characteristic information on a plurality of positions in the object to be acquired.

CITATION LIST

Patent Literature

[PTL 1]
Japanese Patent Application Laid-open No. 2010-022812

SUMMARY OF INVENTION

Technical Problem

Object information is acquired by executing reconstruction processing on signal data on acoustic waves received by a plurality of acoustic wave receiving elements. Examples of the reconstruction processing include data processing represented by back projection in a time domain or a Fourier domain, or delay-and-sum technique. These types of processing generally involve a high computational complexity. Thus, when generating object information following reception of acoustic waves, it is difficult to visualize object information following reception of acoustic waves in line with demands for an enhanced definition of images and an increased frequency of light irradiation.

The present invention has been developed in connection with the above-described problems. An object of the present invention is to improve, in photoacoustic measurement, following capability of visualization of object information to acquiring of signal data.

Solution to Problem

The present invention provides an object information acquiring apparatus comprising:
a processor configured to generate image data representing characteristic information on an object, based on signals acquired by receiving an acoustic wave generated from an object by a plurality of times of light irradiation to the object; and
a display controller configured to allow a display to display an image based on the image data, wherein
the display controller is configured to perform first display in which an image is displayed in parallel with irradiation with the light and reception of the acoustic wave and second display in which an image is displayed based on more signal than in the first display, and
the processor is configured to acquire the characteristic information for a smaller number of units of reconstruction when generating image data used for the first display than when generating image data used for the second display.

The present invention also provides a signal processing method comprising:
a step of generating image data representing characteristic information on an object, based on signals acquired by receiving an acoustic wave generated from an object by a plurality of times of light irradiation to the object; and
a step of displaying an image based on the image data on a display, wherein
the step of displaying includes performing first display in which an image is displayed in parallel with irradiation with the light and reception of the acoustic wave and second display in which an image is displayed based on more signals than in the first display, and
the step of generating includes generating the characteristic information for a smaller number of units of reconstruction when generating image data to be used for the first display in the step of generating than when generating image data to be used for the second display in the step of generating.

Advantageous Effects of Invention

The present invention allows, in photoacoustic measurement, following capability of visualization of object information to acquiring of signal data can be improved.

Further features of the present invention will become apparent from the following description of exemplary embodiments with reference to the attached drawings.

DESCRIPTION OF EMBODIMENTS

A preferred embodiment of the present invention will be described below with reference to the drawings. Dimensions, materials, shapes, relative arrangement, and the like of components described below are to be changed according to a configuration of an apparatus to which the invention is applied and various conditions for the apparatus. Therefore, the scope of the invention is not intended to be limited to the following description.

The present invention relates to a technique for detecting acoustic waves propagating from an object to generate and acquire characteristic information on the interior of the object. Therefore, the present invention is considered to be an object information acquiring apparatus or a control method therefor, or an object information acquiring method and a signal processing method. The present invention is also considered to be a program that allows the methods to be executed by an information processing apparatus including hardware resources such as a CPU and a memory, or a storage medium that stores the program.

The object information acquiring apparatus in the present invention includes an apparatus that utilizes a photoacoustic effect to irradiate an object with light (electromagnetic wave) and receive acoustic waves generated in the object to acquire characteristic information on the object as image data. In this case, the characteristic information is information that is generated using receive signals obtained by receiving photoacoustic waves and that includes characteristic values corresponding to a plurality of positions in the object.

The characteristic information acquired by photoacoustic measurement includes values reflecting a light energy absorptance. For example, the information includes a source of acoustic waves based on irradiation with light, an initial sound pressure in the object, or an optical energy absorption density or absorption coefficient derived from the initial sound pressure or the concentrations of substances contained in a tissue. When an oxyhemoglobin concentration and a reduced hemoglobin concentration are determined as the concentrations of substances, an oxygen saturation distribution can be calculated. Furthermore, a glucose concentration, a collagen concentration, a melanin concentration, volume fractions of fat and water, and the like are determined.

Based on characteristic information for each position in the object, a two- or three-dimensional characteristic information distribution is obtained. Distribution data may be generated as image data. Characteristic information may be determined as distribution information for the different positions in the object rather than as numerical data. That is, the characteristic information may be distribution information such as an initial sound pressure distribution, an energy absorption density distribution, an absorption coefficient distribution, or an oxygen saturation distribution.

Acoustic waves as used herein typically refer to ultrasonic waves and include elastic waves referred to as sound waves or acoustic waves. Electric signals into which acoustic waves are converted by transducers or the like are also referred to as acoustic signals. However, the description "ultrasonic wave" or "acoustic wave" herein is not intended to limit the wavelengths of these elastic waves. Acoustic waves generated based on the photoacoustic effect are referred to as photoacoustic waves or optical ultrasonic waves. Electric signals derived from photoacoustic waves are referred to as photoacoustic signals.

As described in embodiments in detail, the present invention is characterized in that, for an object information acquiring apparatus that allows visualization of object information to follow acquired signal data on acoustic waves, following capability of the visualization to acquiring of signal data is improved. The same components are in principle denoted by the same reference numerals, and description of these components is omitted.

Embodiment 1

In the present embodiment, a method for an apparatus utilizing the photoacoustic effect will be described in which visualization of object information is allowed to more appropriately follow acquired signal data in acoustic waves.

Basic Configuration of the Apparatus

Figure 1:
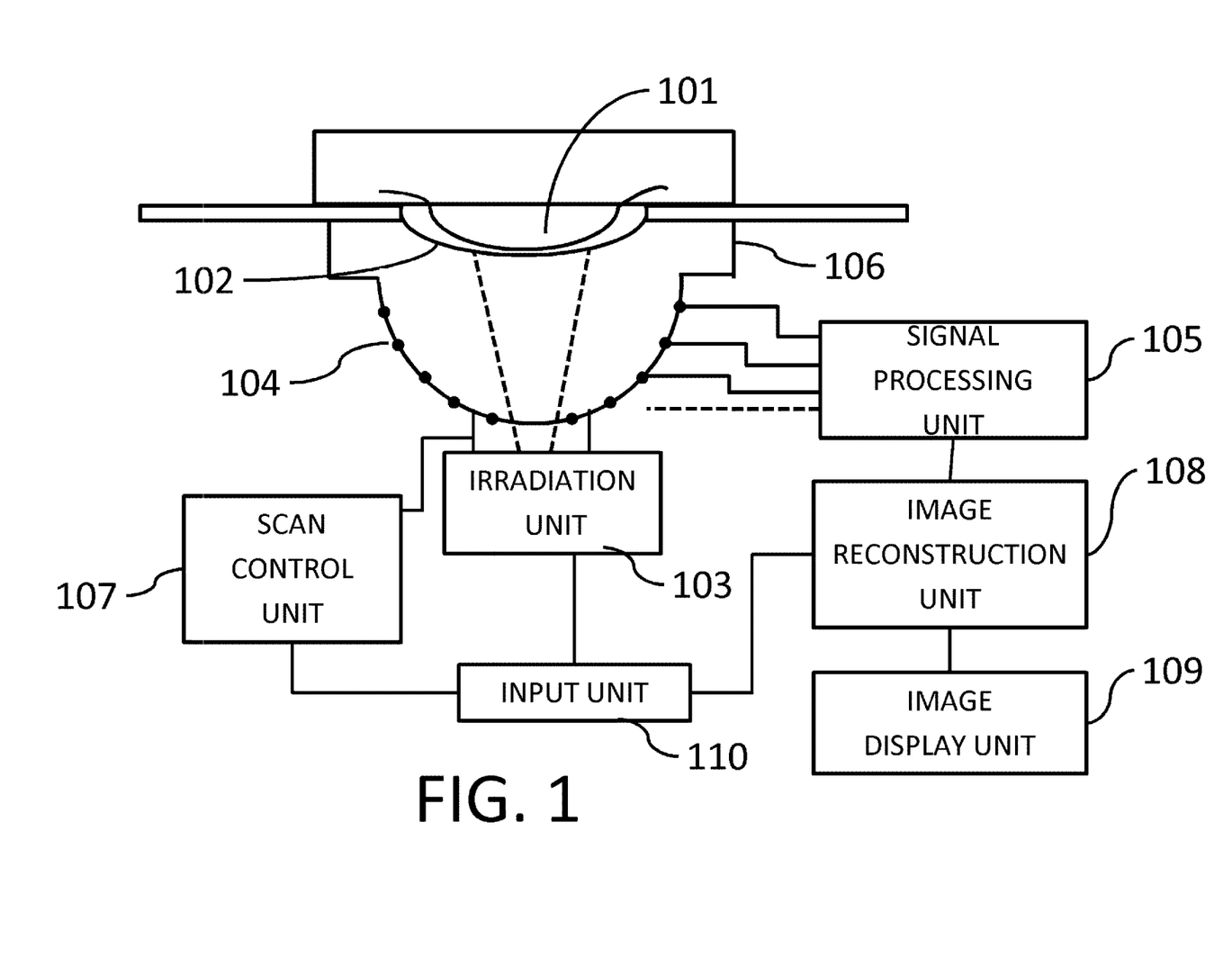
FIG. 1 is a block diagram of an object information acquiring apparatus.

FIG. 1 is a block diagram depicting a configuration of an object information acquiring apparatus in Embodiment 1. The apparatus has an object holding unit 102 for holding a living organism 101 that is an object, an irradiation unit 103 that radiates light, and transducers 104 each of which receives and converts an acoustic wave into a receive signal. The apparatus further has a signal processing unit 105 for amplifying and converting the receive signal into a digital signal, a supporter 106 that supports at least some of the plurality of transducers 104 such that directions in which the transducers are most sensitive in connection with reception directivity intersect one another. The apparatus further has a scan control unit 107 that implements control of scanning by the irradiation unit 103 and the supporter 106 and an image reconstruction unit 108 that generates image data for different regions for the respective wavelengths of light radiated from the irradiation unit 103 using signals from a signal processing unit 105. The apparatus further includes an image display unit 109 for adding up generated images together for display and an input unit 110 for setting, for instance, conditions for image capturing and starting image capturing. The components will be described below, and finally, a step for allowing imaging to follow acquired data more appropriately so as to improve following capability of the visualization to acquisition of signal data will be described.

Object Holding Unit

The living organism 101 may be, for example, a breast. The object holding unit 102 is positioned on an optical path of light and is thus preferably formed of a material such as polymethyl pentene which has a high transmittance with respect to light used. Furthermore, in order to enhance ultrasonic-wave transmissivity or to reduce harmful noise, the object holding unit 102 is preferably thin. Therefore, the object holding unit 102 may be a member that is strong enough to bear the weight of the object in spite of the thinness of the member. Additionally, the object holding unit 102 is preferably a member that is acoustically compatible with the transducers 104. Specifically, a bowl- or dish-shaped member formed of PET may be utilized. Alternatively, a stretchable film-like member may be used.

The space between the object holding unit 102 and the object is preferably filled with a matching liquid for matching of acoustic impedance. The matching liquid preferably has an acoustic impedance close to the acoustic impedance of human bodies and causes ultrasonic waves to be only insignificantly attenuated. For example, water, gel, or castor oil may be used.

Irradiation Unit

The irradiation unit 103, which irradiates the living organism 101 with light, includes a light source that generates light and an irradiator that guides and radiates light from the light source to the living organism. The light source is preferably a solid laser that can generate pulsed light (a pulse width of 100 nsec or less) having a central wavelength in a near infrared region of 530 to 1300 nm. For example, a yttrium-aluminium-garnet laser or a titanium-sapphire laser is used. The wavelength of measurement light is selected between 530 nm and 1300 nm according to a light absorbing substance (for example, hemoglobin, glucose, or cholesterol) in the living organism to be measured.

In the present embodiment, two titanium-sapphire lasers were used to alternately radiate light with a short wavelength of 756 nm and light with a long wavelength of 797 nm at 10 Hz. More preferably, the wavelength of pulsed light is set within the range from approximately 700 nm to approximately 1200 nm, which corresponds to the near infrared region, which is referred to as an optical window. Light in this region reaches a relatively deep portion of the living organism and thus allows information for the deep portion of the living organism to be acquired. When the measurement is limited to a surface portion of the living organism, visible light of approximately 500 to 700 nm and light in the near infrared region may be used. Moreover, the wavelength of the pulsed light is desirably such that an observation target exhibits a high absorption coefficient with respect to the wavelength.

Examples of the irradiator include a mirror that reflects light, a lens that condenses, enlarges, or deforms light, a prism that disperses, refracts, and reflects light, optical fibers through which light propagates, and a diffusor. Any irradiator may be used so long as the irradiator allows light emitted from the light source to be radiated to a desired region of the object so as to have a desired shape. In the present embodiment, an exit end for light from the irradiator is positioned at the bottom of the supporter 106, which is described later, and is moved by controllable movement of the supporter 106 by the scan control unit 107. The position of the exit end is not limited to this so long as the position allows the living organism 101 to be irradiated with light.

Transducers

The transducers 104 are elements that receive and convert an acoustic wave into an electric signal (receive signal). One transducer 104 may include a plurality of elements. The elements provided in the transducers 104 may be conversion elements using a piezoelectric phenomenon, conversion elements using resonance of light, or conversion elements using a variation in capacitance. However, any elements may be used so long as the elements allow an acoustic wave to be received and converted into an electric signal.

Signal Processing Unit

The signal processing unit 105 includes a signal amplifier that amplifies analog signals (analog receive signals) received from the transducers 104 and an A-D converter that converts the analog signals into digital signals. In order to obtain image data with an even contrast in spite of the depth in the living organism, the signal amplifier, for example, controllably increases and reduces amplification gain according to an amount of time from light irradiation until an acoustic wave reaches the element in the transducer. The signal amplifier also corrects a variation in sensitivity among the elements with respect to a digital receive signal and executes complementation processing on physically or electrically defective elements and recording processing on a recording medium (not depicted in the drawings). The signal processing unit 105 can be configured using, for example, a processing circuit including an FPGA.

Supporter

The supporter 106 is a container-like member that supports the transducers 104. The transducers 104 are preferably spirally arranged on an inner surface of the container. Forming the transducer support surface to have a curved surface, a high-resolution region is formed in which high reception sensitivity directions (directional axes) of the respective transducers congregate. The high-resolution region can be defined as a range that is centered around a location where the transducer exhibits the highest resolution and in which the transducer exhibits a resolution that is 50% or more of the highest resolution. The container may be shaped like a hemisphere, a spherical crown, a part of an ellipsoid, a bowl, or a combination of a plurality of flat or curved surfaces.

The space between the interior of the supporter 106 and the object holding unit 102 is preferably filled with a matching liquid for matching of acoustic impedance. The material of the matching liquid may be the same as or may be different from the material used in the object holding unit 102. For example, ultrasonic gel may be applied to the object, and the interior of the supporter may be filled with water.

Scan Control Unit

The scan control unit 107 varies the positions of the light exit end and the supporter 106 relative to the object. For example, the scan control unit 107 may be equipped with a stepping motor or a ball screw and may include a stage that can be subjected to horizontal scans in an X direction and a Y direction. The stage may be controlled using a dedicated processing circuit or an information processing apparatus described below. The stage may be preferably subjected to scans in a Z direction in addition to the horizontal scans in the X direction and the Y direction. The scan control allows information to be acquired over a large area of the object. In particular, when a hemispherical supporter forming the high-resolution region is used, the scan control allows acquisition of high-definition image data for the object as a whole. However, the scan control is not necessarily needed; the scan control is not needed when a region of interest is small. The scan control is not essential to the present invention. The present invention is applicable to all cases where images need to be displayed in real time during photoacoustic measurement.

In the present embodiment, a measurement position is a central position of the supporter 106 at a timing to radiate light. Normally, a propagation speed of acoustic waves is higher than a speed at which the scan control unit 107 moves the supporter 106. Thus, an acoustic wave may be considered to be received at the position of the transducer 104 at the time of light irradiation. Thus, in the present embodiment, the timing to radiate light corresponds to a timing to measure acoustic waves. Furthermore, the positions of the plurality of transducers 104 on the supporter 106 are known. Therefore, image reconstruction for any region can be achieved based on the position of the supporter 106 and the light irradiation timing. For a relation between the scan control and the light irradiation and acoustic-wave reception, continuous scanning or step-and-repeat may be used. The scan control unit corresponds to a scan controller in the present invention.

Image Reconstruction Unit

The image reconstruction unit 108 acquires optically characteristic information for each position in the living organism 101 using signals output from the signal processing unit 105. A characteristic information distribution (an absorption coefficient distribution, an oxygen saturation distribution, or the like) can be generated as image data. Various types of correction processing such as adjustment of brightness, distortion correction, and clipping of a region of interest may be applied to generated image data to generate image data preferable for diagnosis. As the image reconstruction unit 108, an information processing apparatus (a PC, a workstation, and the like) may be utilized which includes resources such as a CPU, a memory, and a communication apparatus and which operates in accordance with programs. The image reconstruction unit 108 functions as a processor and display controller in the present invention.

Image reconstruction can be performed using any known algorithm (delay-and-sum, Fourier transform, a repeated computation method, or the like). More specifically, in the image reconstruction, the image reconstruction unit 108 performs image reconstruction based on digital electric signals to acquire characteristic information, for each of a plurality of units of reconstruction, on the interior of the object. The units of reconstruction are regions each with any size into which the region of interest that is an imaging target inside the object is divided. The unit of reconstruction is referred to as a voxel when three-dimensional image data is generated and as a pixel when two-dimensional image data is generated. The three-dimensional (or two-dimensional) image data is indicative of the distribution of characteristic information in the units of reconstruction arranged in a three-dimensional (two-dimensional) space. In sequential display described below, computational complexity may be reduced by setting a larger unit of reconstruction than in high-definition display. Furthermore, a method with a low computational complexity may be utilized for the sequential display, and repeated computation with a relatively high computational complexity may be utilized for the high-definition display. In the specification, the sequential display is also referred to as first display, and the high-definition display is also referred to as second display.

Reconstruction Mode Switching

In the present embodiment, which of the sequential display mode and the high-definition display mode is used for the image reconstruction can be selectively determined. In the sequential display, images are displayed in parallel with the light irradiation and the acoustic-wave reception. The sequential display is suitable for real-time display performed in parallel with the photoacoustic measurement. In the sequential display, image data is generated at high speed based on a relatively small number of electric signals. However, disadvantageously, image quality is low, and images fail to reflect the overall configuration of the object. On the other hand, in the high-definition display, image data is generated based on more electric signals than in the sequential display. Consequently, high-quality images of large regions can be generated. That is, compared to the sequential display, the high-definition display involves generation of image data with an increased total amount of data in electric signals used for image generation. Even when the same electric signal as that used for the sequential display is repeatedly used, images are generated based on more electric signals than in the sequential display.

During the high-definition display, characteristic information for units of reconstruction for a large area of the object (for example, the entire region of interest) is acquired to allow three-dimensional image data to be reconstructed. On the other hand, during the sequential display, characteristic information for a narrower area (for example, a part of the region of interest that is designated by a user) is acquired. Furthermore, during the sequential display, three-dimensional image data may be projected using a predetermined technique and displayed as two-dimensional images. For example, maximum intensity projection (MIP) may be applied to reconstructed characteristic information to generate MIP images. Any projection direction may be set. For example, when the supporter is scanned in the X direction and the Y direction, two-dimensional images can be generated by projection in the Z direction orthogonal to the scanning direction. Even in the high-definition display, three-dimensional image data may be displayed as two-dimensional images by projection using a predetermined technique.

The type of characteristic information may be switched between the sequential display and the high-definition display. In this case, during the sequential display, an initial sound pressure distribution is displayed which can be acquired by simple reconstruction or a light energy absorption density distribution is displayed which can be acquired using a Gruneisen coefficient taking a predetermined value for each object. On the other hand, during the high-definition display, an absorption coefficient distribution can be displayed which needs computation based on a light quantity distribution. Furthermore, during the high-definition display, computational resources can be easily provided which are needed to display an oxygen saturation distribution.

Additionally, in the sequential display, electric signals derived from light with a plurality of wavelengths can be utilized for image reconstruction at different depths. Here, the light source is assumed to be able to radiate light with a first wavelength and light with a second wavelength different from the first wavelength. Then, since the light transmittance inside the object varies according to the wavelength, a first region inside the object can be imaged using an electric signal derived from the light with the first wavelength, and a second region different from the first region can be imaged using an electric signal derived from the light with the second wavelength. Typically, the depth in the object that can be reached by light increases consistently with the wavelength of the light, and thus, the first region and the second region, which is deeper (which is farther from the light source) than the first region, can be suitably imaged by setting the second wavelength larger than the first wavelength.

The computational complexity in the sequential display varies according to conditions such as a computation time determined by a scan speed, the size of the unit of reconstruction, and the size of the object region that is a basis for acquisition of characteristic information. Therefore, as and when these conditions permit, in the sequential display, the initial sound pressure may be standardized based on a light quantity distribution to determine the absorption coefficient or the oxygen saturation. The value of the initial sound pressure varies significantly according to a distance from the light source (in other words, the amount of light attenuation after irradiation). Thus, when the maximum value is extracted in order to generate an MIP image or when an electric signal derived from light with a plurality of wavelengths is utilized for image reconstruction at different depths, computed values may disadvantageously be less correct. Thus, the above-described standardization allows this problem to be solved. However, the standardization involves an increase in computational complexity, and thus, whether or not to execute the standardization is to be determined particularly in view of a relation with the scan speed.

The image reconstruction unit 108 in the present embodiment acquires characteristic information for different regions for the respective wavelengths emitted from the irradiation unit 103. That is, the characteristic information for the first region is acquired based on an electric signal derived from a photoacoustic wave resulting from irradiation of the object with the light with the first wavelength. The characteristic information for the second region is acquired based on an electric signal derived from a photoacoustic wave resulting from irradiation of the object with the light with the second wavelength.

Figure 2A:
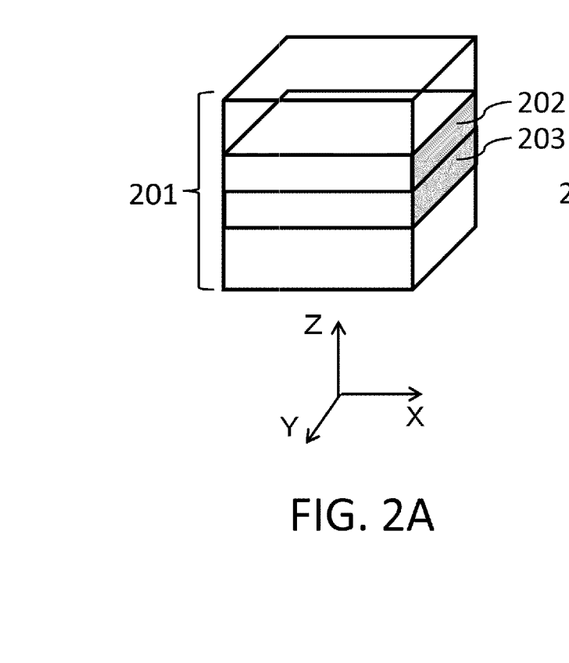
FIGS. 2A to 2C are image diagrams depicting regions that are a basis for image data generation for sequential display.

In the present embodiment, light with a small wavelength of 756 nm and light with a large wavelength of 797 nm are alternately radiated at 10 Hz. FIG. 2A is a schematic diagram of an image formation region in the present embodiment. An image reconstruction region 201 corresponds to the entire target region (the region of interest) for photoacoustic measurement. Light is radiated from an upper part of the figure along the Z axis. The image reconstruction region 201 is divided into voxels with a desired pitch (not depicted in the drawings). A small-wavelength reconstruction region 202 is a region (first region) reconstructed using a receive signal derived from light with a small wavelength (first wavelength). A large-wavelength reconstruction region 203 is a region (second region) reconstructed using a receive signal derived from light with a large wavelength (second wavelength) that can reach a larger depth. In real-time display, the entire images of the reconstructed first region and second region may be displayed or the maximum intensity projection may be applied to the respective areas.

A preferable signal processing method in this case is a technique in which, in the high-definition display, the oxygen saturation is computed and displayed for a portion in which the small-wavelength reconstruction region corresponding to the first wavelength overlaps the large-wavelength reconstruction region corresponding to the second wavelength. This is because the high-definition display allows for a relatively long processing time. On the other hand, in the sequential display, the wavelengths overlap in few regions (or no regions). Thus, since acquiring the oxygen saturation using two wavelengths is difficult, information such as an initial sound pressure distribution, a light energy absorption density, or an absorption coefficient distribution may be displayed which can be acquired even using a single wavelength.

The image reconstruction unit 108 in the present embodiment limits the reconstruction region for each wavelength, reducing the computation complexity in reconstruction for each light irradiation. As a result, the computation time can be reduced, allowing image display to follow acquired signal data on acoustic waves more appropriately. Therefore, real-time display can be suitably performed in which images are generated with photoacoustic measurement and probe scanning in execution. At this time, narrowing the small-wavelength reconstruction region 202 and the large-wavelength reconstruction region 203 allows images to be displayed at a higher speed.

In general, for living organisms, light with a larger wavelength is said to be able to reach a deeper position. Thus, when the region to be reconstructed is allocated according to the measurement depth for each wavelength, the quality of images displayed by the image display unit 109 described below is improved. In this case, a value is set which allows imaging to follow acquired signal data on acoustic waves more quickly. Therefore, when the scans end, all the regions of the object are preferably subjected to image reconstruction. Characteristic information is acquired for more units of reconstruction at least than in the real-time display.

The depths of the first region and the second region from the body surface (in other words, the distance from the light source) can be optionally set. Typically, when the object is the breast, a depth at which the breast cancer is likely to be developed may be set. The depth of the breast cancer varies according to the type and extent of the breast cancer, the size of the breast, the thickness of fat, and the like. For example, the region may be set several cm (typically 2 or 3 cm) below the body surface.

In the present embodiment, for light with two wavelengths, images of different regions are reconstructed. However, even when light with three or more wavelengths is dealt with, different regions can be reconstructed.

Image Display Unit

The image display unit 109 displays images based on image data received from the image reconstruction unit 108. The image display unit 109 corresponds to a display in the present invention. During the sequential display, the small-wavelength reconstruction region 202 and the large-wavelength reconstruction region 203 are added up for display of image data to enable an increase in the amount of information for the sequential display. The add-up of image data refers to generation of such image data as allows a large area of each image to be displayed based on images of different regions generated based on each wavelength. For an overlap portion in which the regions partly overlap, weighted average processing or the like is preferably used to prevent the user from feeling uncomfortable.

Input Unit

The input unit 110 receives instructions provided to the apparatus by the user. Input instructions include an image taking start command, designation of a region of interest, a reconstruction range or reconstruction image quality in the sequential display, a scan region in the scan control, and the wavelength of light. As the input unit 110, a pointing device such as a mouse or a keyboard, a pen tablet, a keyboard, a sound input apparatus, or the like may be utilized. Furthermore, when the image display unit 109 includes a touch input function, the input unit 110 may be utilized to receive instruction inputs. The input unit corresponds to an input unit in the present invention.

Furthermore, the user can use the input unit 110 to designate the region of interest for photoacoustic measurement with reference to the living organism 101. In that case, the scan control unit 107 controls the scan position of the supporter 106 so as to allow acquisition of an acoustic wave from the region of interest.

The input unit 110 also receives the input of information regarding which region is to be reconstruct at which wavelength and the range of reconstruction based on each wavelength. Based on those pieces of information, the image reconstruction unit 108 reconstructs an electric signal derived from a photoacoustic wave resulting from light with each wavelength. However, with respect to which region is to be reconstructed at which wavelength and the range of reconstruction, the image reconstruction unit 108 may store set values. When the apparatus receives an image-taking instruction from the user, the scan control unit 107 starts the scan control, and the irradiation unit 103 starts laser irradiation. Furthermore, when a reconstruction region is designated for the sequential display, the image reconstruction unit may determine the wavelength corresponding to the depth of the reconstruction region.

Flow in the Present Embodiment

Figure 3:
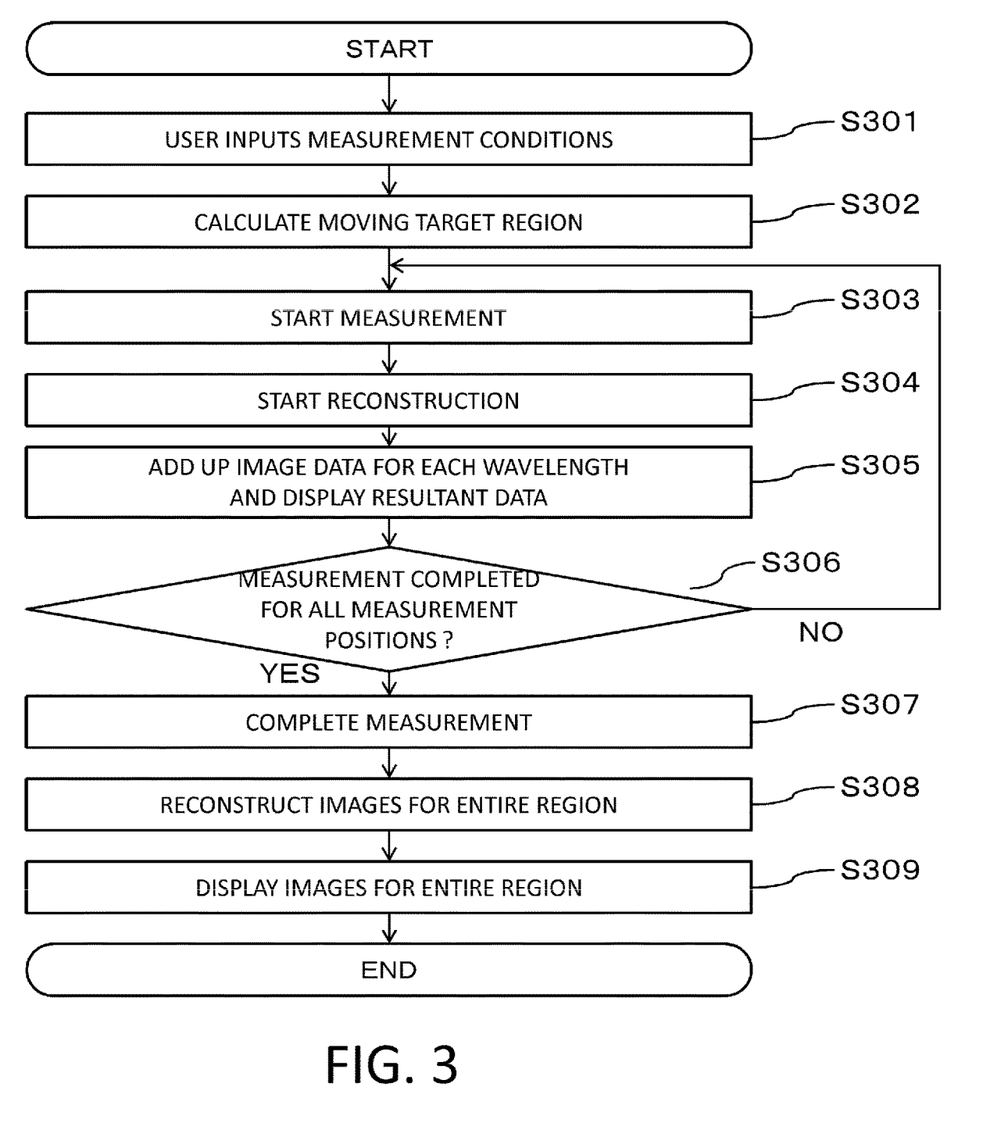
FIG. 3 is a flowchart illustrating an example in which an image is divided into reconstruction regions for every plurality of wavelengths.

The present embodiment is executed according to a flow illustrated in FIG. 3. The flow starts when the living organism 101 is held by the object holding unit 102.

In step S301, conditions for measurement are set. For example, using the input unit, the user inputs information on the object, the type of the object holding unit 102, an imaging region, and regions in the imaging region for the respective wavelengths that are reconstructed by the image reconstruction unit 108. Alternatively, the conditions may be read from the memory.

Figure 4:
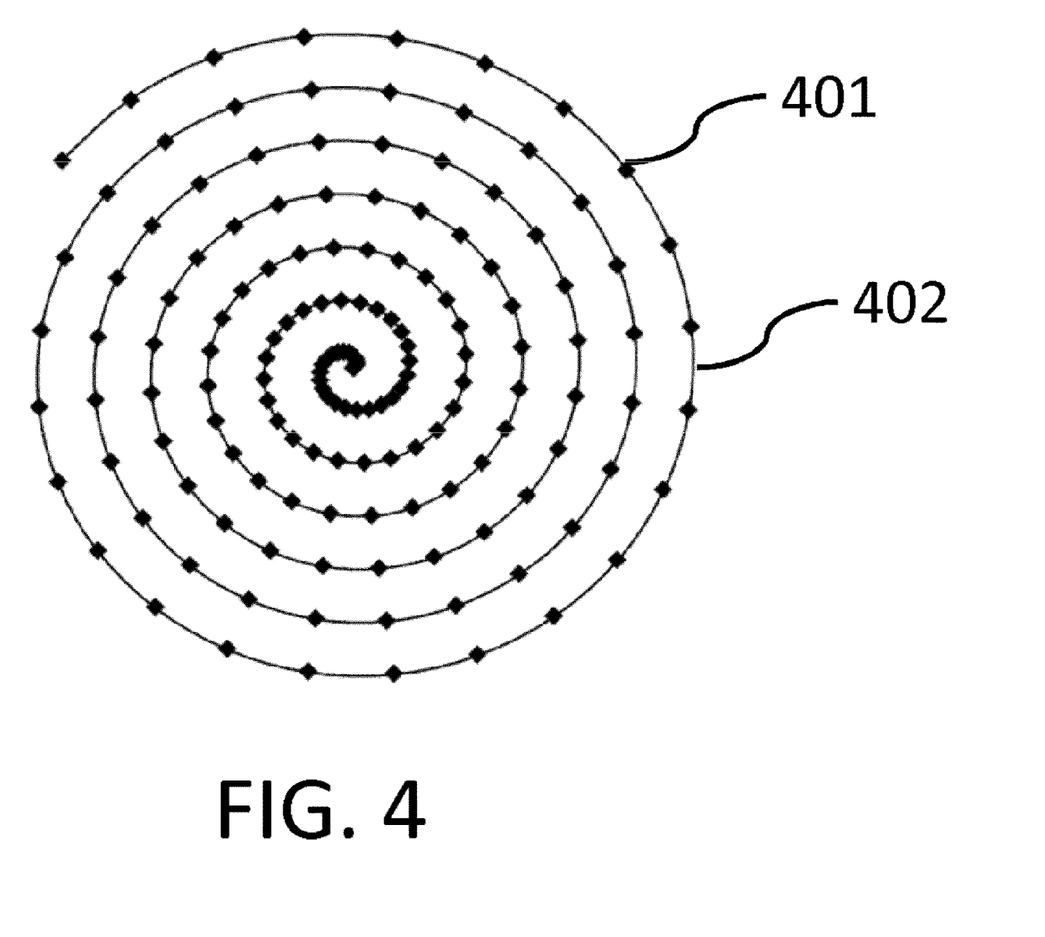
FIG. 4 is an image diagram of a driving control pattern of transducers and light exit end.

In step S302, the scan control unit 107 computes driving conditions for the supporter 106 based on the measurement conditions input in step S301. The supporter 106 is desirably moved such that all of the imaging region is encompassed by a high-resolution region where directions in which the transducers 104 exhibit high reception sensitivity intersect one another. In the present embodiment, the region of interest is subjected to spiral horizontal scans in the X direction and the Y direction as depicted in FIG. 4. In FIG. 4, reference numeral 402 denotes a trajectory of a central portion of the supporter, and reference numeral 401 denotes the positions where light irradiation and acoustic-wave reception are started.

The driving as described above enables a reduction in ripple of the surface of the matching liquid. Furthermore, even when the region of interest is changed, this can be dealt with by changing the size of a circle for spiral driving. The scan control is not limited to the above-described method so long as the scan control enables a change in the relative position between the supporter 106 and the object. For example, the object may be moved or both the object and the supporter may be moved.

In the present embodiment, the supporter 106 is continuously moved. However, a step-and-repeat method may be used in which the supporter 106 is moved and stopped repetitively so that light irradiation and acoustic-wave reception are performed at the position where the supporter 106 is stopped. Furthermore, the driving is not limited to the spiral path. Any path may be used for the driving so long as the supporter 106 can be driven so as to allow the high-resolution region to encompass the entire region of interest. For example, a raster scan method may be used in which main scans and sub-scans are repeated.

In step S303, an instruction to start imaging transmitted from the input unit 110 is received. Consequently, the scan set in S302 is started. Furthermore, the scan involves irradiation with light with a plurality of wavelengths emitted from the irradiation unit 103, reception of photoacoustic waves by the transducers 104, and digital conversion and amplification processing executed by the signal processing unit 105. Any method may be used to synchronize these processes. For example, a possible method may include storing digital signals in accordance with photodetection using a photodetector or in conjunction with control signals for light irradiation. Additionally, preferably, coordinate information for the scan control unit 107 is acquired based on, for example, control information for an XY stage to store positions where the respective digital signals are acquired.

In step S304, the image reconstruction unit 108 reconstructs regions according to each wavelength. Which wavelength a specific signal has been generated from is determined, for instance, based on information on control of irradiation with light with each wavelength performed by the irradiation unit 103. Furthermore, index information indicative of a wavelength may be added to signals transmitted from the signal processing unit 105. The image reconstruction unit 108 images predetermined regions according to the wavelength and transmits resultant data to the image display unit 109.

In step S305, the image display unit 109 displays image data for each wavelength transmitted from the image reconstruction unit 108. Consequently, the image data can be displayed so as to follow driving of the supporter 106. In the present step, preferably, images corresponding to the high-resolution region are gradually added as the scan progresses, leading to enlargement of the entire image. In this case, according to changes in relative position, images based on newly generated image data are added to displayed images.

In step S306, the process determines whether signals have been successfully acquired at all measurement positions in the region of interest. If not all the signals have been acquired, the processing starting at step S303 is repeated. If all the signals have been acquired, the process proceeds to step S307 to end the scans. Then, the photoacoustic measurement is completed. The sequential display mode is thus ended, and the high-definition display mode is subsequently started.

In step S308, the image reconstruction unit 108 performs image reconstruction on the entire region of interest. However, reconstruction of the entire region of interest need not necessarily be performed immediately after the end of the scans. All the acquired data may be transferred to an external storage apparatus, such as an HDD or a flash memory, or a server so that the reconstruction can be performed in the user's desired place at the user's desired time. The present step is sufficient so long as the step at least allows more information to be obtained than the sequential display.

In step S309, the images reconstructed in S308 are displayed on the image display unit 109. In S309, image reconstruction processing is executed on all the received signals, providing images having a higher definition than in S305. Furthermore, images involving high computational complexity are obtained such as an absorption coefficient distribution and an oxygen saturation distribution.

When the above-described flow is executed using the apparatus in the present invention, image display can be performed so as to appropriately follow scans in the sequential display, which is performed in real time in parallel with the scans. After the scans are ended, images can be displayed with a high definition. Therefore, in the photoacoustic measurement, visualization of object information is allowed to more appropriately follow acquired signal data.

Variations

Figure 2B:
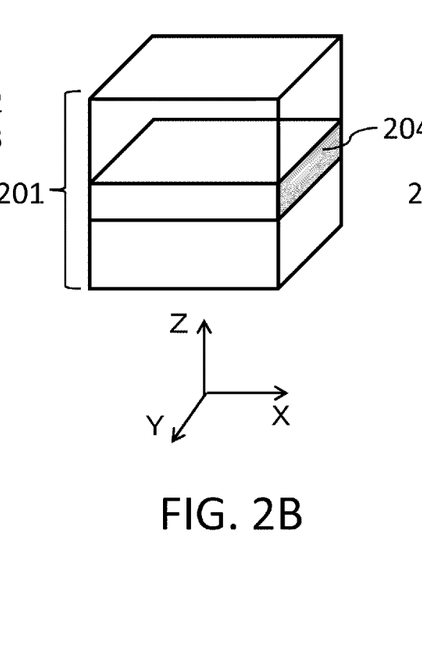

The above-described flow uses light with a plurality of wavelengths. However, as depicted in FIG. 2B, the present invention is applicable to imaging using light with one wavelength. Even in this case, in the sequential display, the computational complexity in the real-time image display can be reduced by performing image reconstruction on a relatively small region (reference numeral 204). On the other hand, in the high-definition display, image reconstruction is performed on the entire region of interest (image reconstruction region 201). As a result, the visualization can be allowed to follow acquired signal data more appropriately.

Figure 2C:
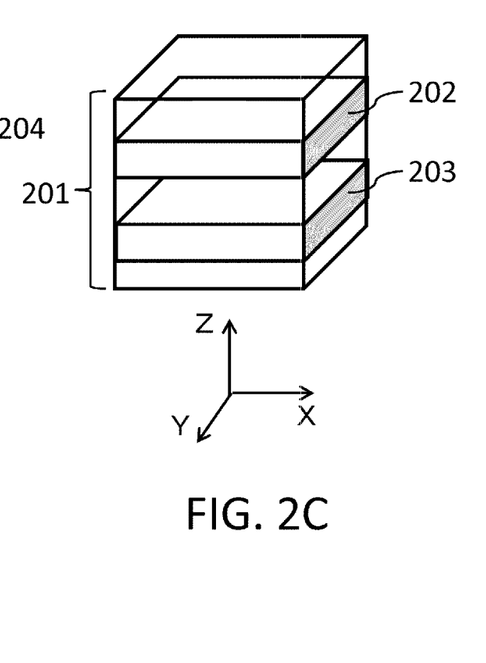

Furthermore, the first region and the second region may be set a distant position as depicted in FIG. 2C. The position of each region can be flexibly set according to the wavelength of light and the imaging region desired by the user.

Embodiment 2

In Embodiment 2, image display is achieved in a shorter time by differentiating the region to be reconstructed and varying the size of the voxel for reconstruction, for each wavelength. In the present embodiment, the amount of time from driving of the supporter 106 until image display is further reduced. The apparatus configuration in the present embodiment is similar to the apparatus configuration in Embodiment 1 except for the functions of the image reconstruction unit 108 and the input unit 110. Description of components similar to the corresponding components of Embodiment 1 is omitted, and only differences from Embodiment 1 will be described in detail.

In the present embodiment, the input unit 110 receives a voxel size for image reconstruction for each wavelength. The image reconstruction unit 108 reconstructs image data into a set size. Consequently, the image data can be transmitted to the image display unit 109 in a reduced time.

Figure 5:
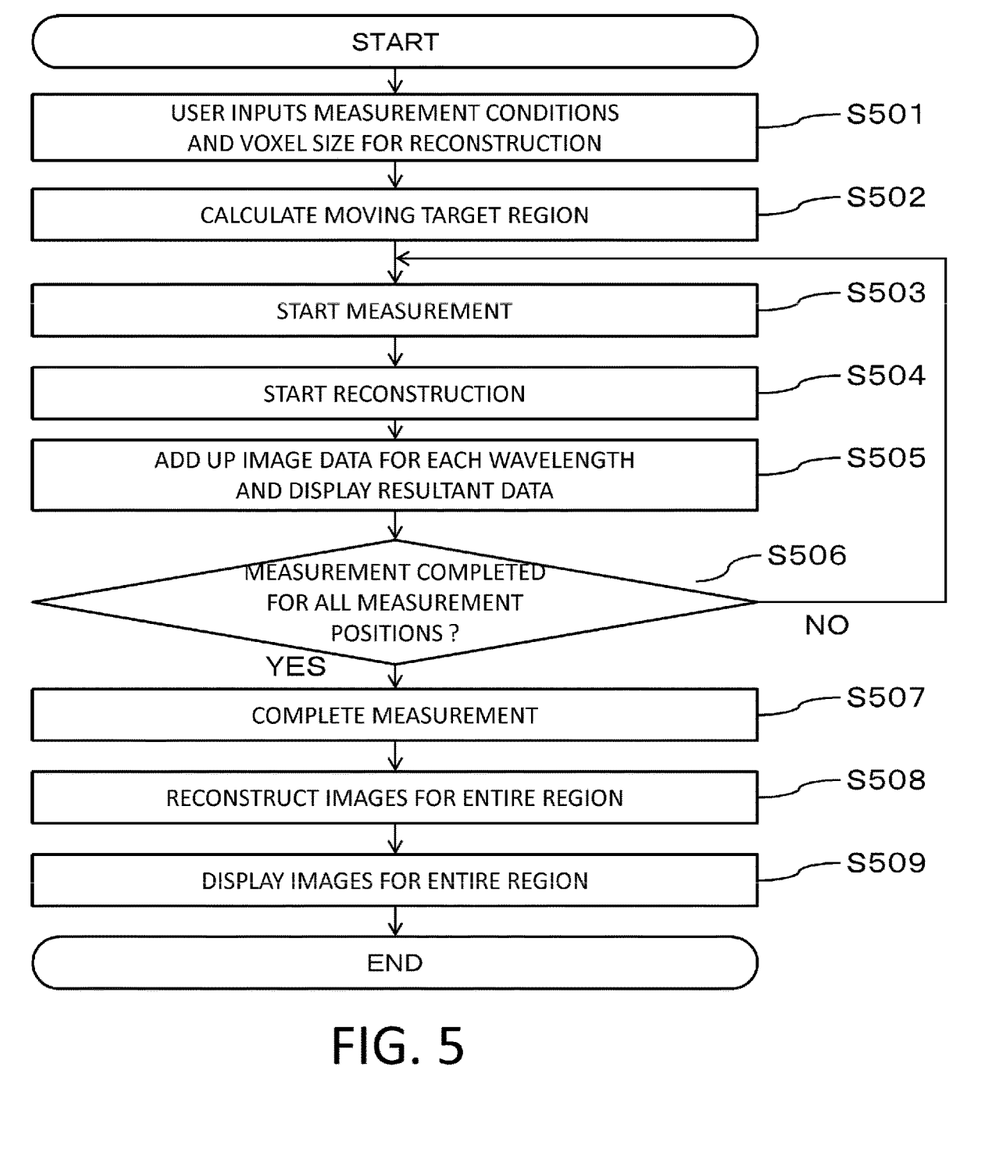
FIG. 5 is a flowchart illustrating an example in which a voxel size is changed.

FIG. 5 is a flowchart of operations in the second embodiment. Steps S502 to S509 are similar to steps S302 to S309 in Embodiment 1. In step S501, the input unit 110 receives a voxel size for reconstruction input by the user. At this time, the voxel size may be varied according to the wavelength. Furthermore, different voxel sizes may be set for the sequential display and for the high-definition display. Furthermore, the user may specify image quality, and the voxel size needed for the image reconstruction unit 108 is calculated to achieve the specified image quality.

In the present embodiment, a large voxel size can be set for the sequential display. As a result, the computational complexity is reduced to allow reconstructed images to be more appropriately displayed in real time.

OTHER EMBODIMENTS

The present invention can be implemented by processing in which a system or an apparatus is supplied via a network or a storage medium with a program that implements one or more functions of the above-described embodiment so that one or more processors in a computer in the system or the apparatus reads and executes the program. Alternatively, the present invention can be implemented by a circuit (for example, an ASIC) that implements one or more functions.

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2016-009864, filed on Jan. 21, 2016, which is hereby incorporated by reference herein in its entirety.

The invention claimed is:

1. An object information acquiring apparatus comprising:
    a processor configured to generate image data representing characteristic information on an object, based on signals acquired by receiving an acoustic wave generated from an object by a plurality of times of light irradiation to the object; and
    a display controller configured to allow a display to display an image based on the image data, wherein
    the display controller is configured to perform first display in which an image is displayed in parallel with irradiation with the light and reception of the acoustic wave and second display in which an image is displayed based on more signal than in the first display, and
    the processor is configured to acquire the characteristic information for a smaller number of units of reconstruction when generating image data used for the first display than when generating image data used for the second display.

2. The object information acquiring apparatus according to claim 1, wherein the processor is configured to generate the characteristic information for three-dimensionally arranged units of reconstruction, and during the first display, generate the image data by projecting the characteristic information acquired with the small number of units of reconstruction.

3. The object information acquiring apparatus according to claim 2, further comprising
    a transducer configured to receive the acoustic wave generated in the object irradiated with light and output the signal, and
    a scan controller configured to scan the transducer in a predetermined direction, wherein
    during the first display, the processor is configured to generate the image data by projecting the characteristic information in a direction orthogonal to the predetermined direction.

4. The object information acquiring apparatus according to claim 2, wherein, during the first display, the processor is configured to generate the image data by applying maximum intensity projection to the characteristic information.

5. The object information acquiring apparatus according to claim 1, wherein the processor is configured to acquire as the characteristic information, during the first display, an initial sound pressure or an optical energy absorption density for each of the units of reconstruction, and during the second display, an absorption coefficient for each of the units of reconstruction as the characteristic information.

6. The object information acquiring apparatus according to claim 1, wherein the processor is configured to acquire as the characteristic information an absorption coefficient for each of the units of reconstruction.

7. The object information acquiring apparatus according to claim 1, further comprising a light source configured to be capable of radiating light with a first wavelength and light with a second wavelength, which is different from the first wavelength, wherein, during the first display, the processor is configured to use the signal derived from the light with the first wavelength to generate the image data for a first region inside the object, and use the signal derived from the light with the second wavelength to generate the image data for a second region, which is different from the first region.

8. The object information acquiring apparatus according to claim 7, wherein the second wavelength is larger than the first wavelength, and the second region is more distanced from the light source than the first region.

9. The object information acquiring apparatus according to claim 7, wherein, during the first display, the processor is configured to acquire as the characteristic information an initial sound pressure, a light energy absorption density, or an absorption coefficient for the units of reconstruction in each of the first and second regions, on a basis of the signals derived from the light with the first wavelength and the light with the second wavelength respectively.

10. The object information acquiring apparatus according to claim 7, wherein, during the second display, the processor is configured to acquire an oxygen saturation as the characteristic information.

11. The object information acquiring apparatus according to claim 7, further comprising an input unit configured to receive an input of a region, for which the image data is generated, inside the object, wherein the processor is configured to determine a region for which the characteristic information is acquired during the first display based on information received by the input unit, and determine whether the signal derived from the first wavelength or the second wavelength is used to acquire the characteristic information, based on the determined region.

12. The object information acquiring apparatus according to claim 1, further comprising:

a plurality of the transducers arranged so as to form a high-resolution region; and a scan controller configured to change a relative position between the plurality of transducers and the object, wherein the first display is performed in parallel with a change of the relative position.

13. The object information acquiring apparatus according to claim 12, wherein, in the first display, an image based on newly generated image data is added to the displayed image according to a change of the relative position.

14. The object information acquiring apparatus according to claim 1, further comprising an input unit configured to receive an input of a region, for which the image data is generated, inside the object.

15. The object information acquiring apparatus according to claim 14, wherein the input unit is configured to receive an input of a region, for which the characteristic information is acquired, during the first display.

16. The object information acquiring apparatus according to claim 14, wherein the input unit is configured to receive an input of image quality of the image displayed during the first display.

17. The object information acquiring apparatus according to claim 14, wherein the input unit is configured to receive an input of a size of the unit of reconstruction.

18. A signal processing method comprising:

a step of generating image data representing characteristic information on an object, based on signals acquired by receiving an acoustic wave generated from an object by a plurality of times of light irradiation to the object; and a step of displaying an image based on the image data on a display, wherein the step of displaying includes performing first display in which an image is displayed in parallel with irradiation with the light and reception of the acoustic wave and second display in which an image is displayed based on more signals than in the first display, and the step of generating includes generating the characteristic information for a smaller number of units of reconstruction when generating image data to be used for the first display in the step of generating than when generating image data to be used for the second display in the step of generating.

19. A non-transitory computer-readable medium storing a program allowing an information processing apparatus to execute the steps of the signal processing method according to claim 18.

* * * * *